United States Patent [19]

Nishioka et al.

[11] Patent Number: 5,524,440
[45] Date of Patent: Jun. 11, 1996

[54] COMPACT REFRIGERATOR FOR COSMETICS

[76] Inventors: Hajime Nishioka, 3-12, Kamonbayashi-cho, Kamitakano, Sakyo-ku, Kyoto-shi, Kyoto 606, Japan; Shiro Amano, c/o Furuno Electric Co., Ltd. 9-52, Ashihara-cho, Nishinomiya-shi, Hyogo 662, Japan; Noriaki Tsumura, c/o Cosmo Tsumura Co., Ltd. 4-1-116, 3-chome, Kamishinden, Toyonaka-shi, Osaka 565, Japan

[21] Appl. No.: 395,634

[22] Filed: Feb. 28, 1995

Related U.S. Application Data

[63] Continuation of Ser. No. 181,866, Jan. 13, 1994, abandoned, which is a continuation of Ser. No. 613,872, Dec. 5, 1990, abandoned.

[30] Foreign Application Priority Data

Feb. 6, 1989 [JP] Japan .................................. 1-12961
Feb. 6, 1989 [JP] Japan .................................. 1-12962

[51] Int. Cl.$^6$ .................................................. F25D 11/00
[52] U.S. Cl. ............................ 62/3.6; 62/3.62; 62/371
[58] Field of Search .................... 62/3.6, 3.62, 3.2, 62/457.1, 457.9, 457.2, 371

[56] References Cited

U.S. PATENT DOCUMENTS

| | | | |
|---|---|---|---|
| 2,932,953 | 4/1960 | Becket et al. | 62/3.6 |
| 3,234,595 | 2/1966 | Weichselbaum et al. | 62/3.6 |
| 3,480,015 | 11/1969 | Gonzalez | 62/3.6 |
| 3,500,649 | 3/1970 | Feldman | 62/3.6 |
| 4,364,234 | 12/1982 | Reed | 62/3.6 |
| 4,393,975 | 7/1983 | Moore | 62/457.2 X |
| 4,584,847 | 4/1986 | Martello et al. | 62/293 |
| 4,706,472 | 11/1987 | Howard | 62/246 |
| 4,823,554 | 4/1989 | Trachtenberg et al. | 62/3.6 |
| 4,892,226 | 1/1990 | Abtahi | 220/412 |

OTHER PUBLICATIONS

Magic Temp manual, Jordan/Fogel Refrigeration Co. Jul. 1978–62;36.
Chillwarmer, advertisement, Caesar, Rivise, Bernstein & Cohen Ltd, Apr. 1980 –62-3.6.

*Primary Examiner*—Henry A. Bennett
*Assistant Examiner*—William C. Doerrler

[57] ABSTRACT

The present invention relates to a compact refrigerator for exclusively storing cosmetic preparations and certain kinds of medicines. Particularly, it relates to a compact refrigerator for storing in the compartment thereof cosmetic preparations not containing any chemical preservative or disinfectant that may have a bad effect on a human body, or cosmetic preparations containing any such preservative or disinfectant only in a small amount, so that any effect produced by the preservative or disinfectant on a human body may be minimized. The refrigerator maintains the temperature in the compartment thereof within a temperature range of about 5° through 10° and keeps them cool. The present invention maintains the temperature in the compartment of the refrigerator within a predetermined range of temperature by means of a thermoelectric module such as a Peltier element and/or a heat dissipating fan.

26 Claims, 3 Drawing Sheets

5,524,440

COMPACT REFRIGERATOR FOR COSMETICS

This application is a continuation of application Ser. No. 08/181,866 filed on Jan. 13, 1994, now abandoned, which is a continuation of application Ser. No. 07/613,872 filed on Dec. 5, 1990, now abandoned.

TECHNICAL FIELD

The present invention relates to a compact refrigerator in which a thermoelectric module, such as a Peltier element, is employed for keeping the temperature in the storage chamber thereof within a predetermined temperature range. Particularly, it relates to a small refrigerator which is used exclusively for storing cosmetic preparations or cosmetics or certain kinds of medicines.

Hereinafter, the present invention will be explained as embodied in a small refrigerator having a storage chamber for storing and keeping cool a cosmetic preparation or a cosmetic not containing any chemical preservatives or disinfectants that may produce a bad effect on a human body, or a cosmetic preparation or a cosmetic containing chemical preservatives or disinfectants only in a small amount, so that any effect as produced by them on a human body may be minimized.

BACKGROUND OF THE INVENTION

Intensive research work has been done on various kinds of cosmetic preparations or cosmetics. There has been conducted a detailed examination on the raw materials thereof, the preservation and disinfection aspects thereof, temperature conditions of a particular cosmetic preparation which give a good feeling to its user and the like. As a result, it has been found that there exists an optimum temperature range which has a significant bearing on the pleasant use of any cosmetic preparation.

BACKGROUND ART

The cosmetic preparations are generally manufactured under semi-sterile conditions, and distributed and sold in properly sealed packages. Therefore, it is usually unlikely that the deterioration or decomposition of any cosmetic preparation may occur as a result of its contamination with microorganisms, such as bacteria or fungi, before it reaches its user. The microbial contamination of the preparation is usually considered to start when the user opens its package and touches the preparation directly. Although such deterioration or decomposition may be more likely to occur during the hot summer season of the year, the propagation of the microorgamisms in the cosmetic preparation which causes its deterioration or decomposition can occur even in winter, as rooms in houses are well heated.

Therefore, the cosmetic preparations generally contain chemical preservatives and disinfectants. Several tens of kinds of chemicals are used as such. The majority of those chemicals are, however, irritant to the skin and can cause skin troubles. As a matter of fact, there is a report showing that even para-hydroxyaminobenzoic ester, which is said to be safer than any other chemicals, has been found to have developed allergy in 0.8 to 9.5% of the patients of contagious skin diseases visiting dermatologists.

The addition of those harmful substances has, however, been considered necessary as a compromise measure for the preservation and disinfection of the cosmetic preparations or cosmetics.

DISCLOSURE OF THE INVENTION

An object of the present invention is to provide a compact refrigerator for storing cosmetic preparations or cosmetics, etc. therein and keeping them cool.

Another object of the present invention is to provide a small refrigerator for storing in the storage chamber thereof and keeping cool any cosmetic preparation or cosmetic not containing any chemical preservatives or disinfectants that may produce bad effects on a human body, or any cosmetic preparation or cosmetic containing any such preservatives or disinfectants only in a small amount, so that any effects produced by them on a human body may be minimized.

Still another object of the invention is to provide a small refrigerator which maintains the temperature in its storage compartment in a temperature range of 5° C. through 10° C., with the storage compartment storing a cosmetic preparation not containing any chemical preservatives or disinfectants that may produce a bad effect on a human body, or a cosmetic preparation containing any such preservatives or disinfectants only in a small amount, so that any effect produced by them on a human body may be minimized.

A further object of the invention is to provide a small refrigerator which is simple in construction, and can effectively maintain the temperature in its storage chamber at a predetermined temperature or in a predetermined temperature range even when a cosmetic preparation or the like is put into or out of the storage chamber.

According to a first aspect of the present invention, there is provided a small refrigerator for cosmetic preparations having a storage chamber in which the temperature therein is maintained within a specific temperature range, with the storage chamber storing a cosmetic preparation not containing any chemical preservatives or disinfectants that may produce bad effects on a human body, or a cosmetic preparation containing any such preservatives or disinfectants only in a small amount, so that any effects produced by them on a human body may be minimized.

According to a second aspect of the invention, there is provided a small refrigerator for cosmetic preparations having a storage chamber in which the temperature therein is maintained in a temperature range of about 5° C. through 10° C., with the storage chamber being defined by a top portion, side portions and a bottom portion and storing a cosmetic preparation not containing any chemical preservatives or disinfectants that may produce a bad effect on a human body, or a cosmetic preparation containing any such preservatives or disinfectants only in a small amount, so that any effect produced by them on a human body may be minimized.

According to a third aspect of this invention, there is provided a small refrigerator for cosmetic preparations having a storage chamber defined by a top portion, sidewall portions and a bottom portion, and comprising a cooling device incorporated in the sidewall portion, a cooling plate located inside the sidewall portion and contacting the cooling device, a heat dissipating plate located outside the cooling device, a cover forming the top portion, a temperature sensor for detecting the temperature in the storage chamber, a fan for promoting the dissipation of heat by means of the heat dissipating plate, and a control device for controlling one or both of the cooling device and the fan in response to output signals of the temperature sensor.

According to a fourth aspect of the invention, there is provided a small refrigerator having a storage chamber defined by a top portion, sidewall portions and a bottom portion, and comprising a cooling device provided in the sidewall portion, a cooling plate located inside the sidewall portion and contacting the cooling device, a heat dissipating plate located outside the cooling device, a cover forming the top portion, a temperature sensor for detecting the temperature in the storage chamber, and a control device for controlling the cooling device in response to an output signal of the temperature sensor.

EMBODIMENTS

Figure 1:
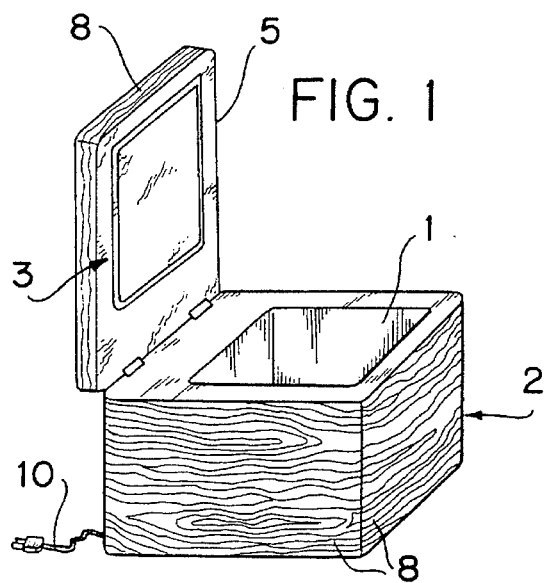
FIG. 1 is a perspective view of an embodiment according to the present invention.
Figure 3:
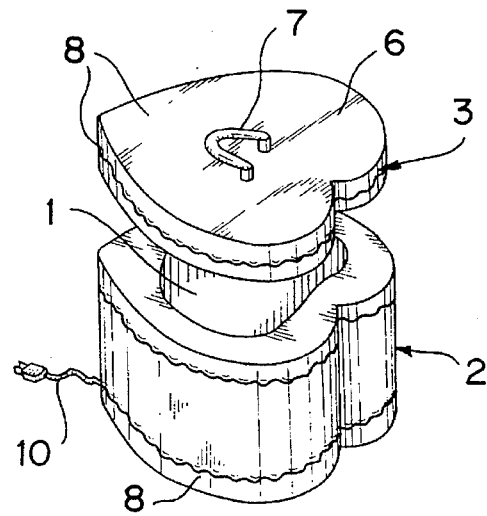
FIG. 3 is a perspective view of an embodiment of the present invention having a top cover.
Figure 2:
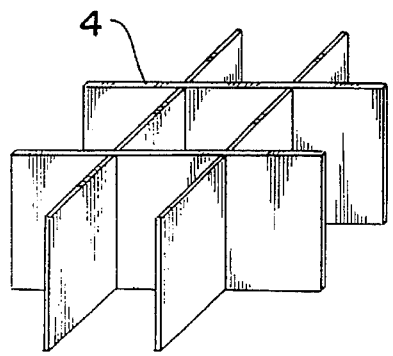
FIG. 2 is a perspective view of an example of partitions.
Figure 4:
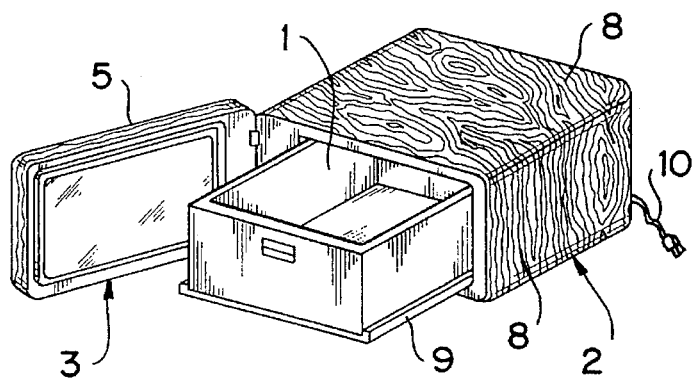
FIG. 4 is a perspective view of another embodiment of the invention.

FIG. 1 is an embodiment of a small refrigerator for cosmetics according to the present invention. A refrigerator 2 has a storage chamber 1 therein. An opening and closing portion 3 of the refrigerator is provided at the top portion or a sidewall portion of the refrigerator 2. Opening and closing means for the refrigerator 2 can be freely chosen and provided. If the opening and closing means is desired to be provided at the top portion of the refrigerator, a door-type cover 5 can be employed as shown in FIG. 1, or a lid-type cover 6 can be provided as shown in FIG. 3. With the refrigerator 2 having the cover door 5 at a sidewall portion, a tray 9 which is slidable on the bottom of the storage chamber 1 can be used for easily putting things into or taking them out of the chamber, as shown in FIG. 4. If necessary, partitions are further used to more effectively utilize the chamber. With regard to the shape of the partitions 4, it is not limited to the one shown in FIG. 2. Other shapes of the partitions can also be designed. Vertical and horizontal planes may be combined to provide partitions as desired, or the whole of the partitions may be formed together and at one time. It is convenient to design the partitions 4 to be removable from the chamber 2 irrespective of the shape thereof. Numeral 10 represents conductive lines for electric power transmission.

Figure 5:
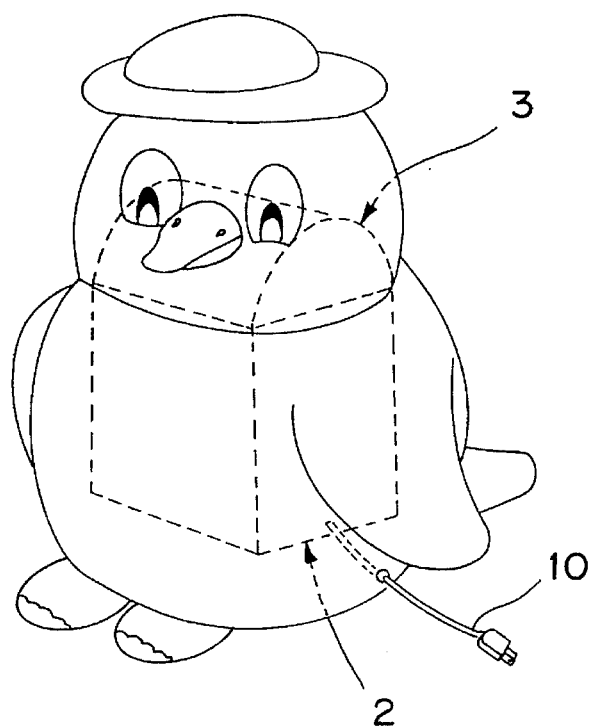
FIG. 5 is a perspective view of another embodiment of the invention in which a refrigerator is included in a toy.

The cooling means is required to constantly maintain the temperature in the storage chamber 1 within a temperature range of about 5° C. through 10° C., as will be explained hereinafter. A cooling method using a compressor and refrigerant or another method using thermoelectric modules such as Peltier cooling elements or the like can be used. The exterior of the refrigerator should be preferably designed so as to give a gorgeous appearance to meet a corresponding surrounding atmosphere existent when the refrigerator is placed on a dresser or a dressing table. Thus, ornamental portion 8 are provided. Ornamental patterns provided on the outer surface of the top portion and sidewall portions of the refrigerator 2 and materials therefor should be attentively chosen. The ornamental portion 8 is provided with a variety of ornamental patterns. The ornamental portion is provided with a grain appearance or a marble appearance or covered with cloth so as to produce a gorgeous appearance. The outer shape of the refrigerator is not limited to that of a substantial parallelepiped like a box. It is also possible to use a container having curved surfaces or a heart-like appearance or to use an animal toy as shown in FIG. 5 in which the refrigerator 2 is included. Also, some portions on the outer surface of the refrigerator 2 can be made irregular to increase aesthetic effects. A handle 7 can be attached on the door 5 or the lid 6 which form the opening and closing portion 3. But, the handle is not the one which is absolutely necessary.

The temperature of the storage chamber 1 plays an important part of the present invention. The temperature in the refrigerator according to the present invention is maintained at a temperature of about 5° C. through 10° C. This temperature limitation is of great significance for the reasons which will hereinafter be explained in detail. Experiments have been made to find out a temperature range which has to be maintained for the proper storage of a cosmetic preparation, such as a lotion or cream, not containing any chemical preservatives or disinfectants. It is important to conduct experiments in terms of the following three factors. More specifically, experiments have been conducted to determine:

(1) The temperature range which is appropriate for preventing the microbial contamination of any such cosmetic preparation and the propagation of microorganisms;

(2) The temperature range in which the viscosity, hardness, etc. of any such cosmetic preparation is appropriate and suitable for satisfactory application; and (3) The temperature range in which any such cosmetic preparation is pleasant to the skin. The results will hereinafter be described.

EXPERIMENT EXAMPLE 1

Experiments for determining the temperature range which is appropriate for preventing the microbial contamination of a cosmetic preparation and the propagation of microorganisms in the preparation:

An emollient lotion was prepared from materials shown in Table 1 in accordance with the recipe also shown in Table 1. No preservatives or disinfectants were used. 0.1 ml of a liquid containing colon bacilli B (WP2, $1.5 \times 10^8$ cells/ml) was put in 1.0 ml of the lotion and the lotion was left to stand at the temperatures of −5° C., 0° C., 5° C., 10° C., 15° C., 20° C., 25° C. and 30° C., respectively, for 14 days in a dark place. Then, the number of the bacilli in the lotion was counted in a dilution thereof. The results are shown in Table 2.

It has become clear that the propagation of bacteria contaminating any such cosmetic preparation can be prevented over a long period of time if it is kept at a temperature not exceeding about 10° C.

TABLE 1

Constituents of an emollient lotion and the proportions thereof.

| Kind | Constituent | Proportion (%) |
| --- | --- | --- |
| Oily constituents | Stearic acid | 2.0 |
| | Cetanol | 1.5 |
| | Vaseline | 3.0 |
| | Lanolin alcohol | 2.0 |
| | Liquid paraffin | 10.0 |
| Emulsifying agent | Polyoxyethylene monooleate | 2.5 |
| Humectants | Glycerin | 3.0 |
| | Propylene glycol | 5.0 |
| Alkali | Triethanolamine | |
| Purified water | | 70.0 |

Process for Preparation

The lotion was prepared by mixing propylene glycol, glycerin and triethanolamine in purified water under heat, adding the other materials, subjecting the mixture to emulsification at 70° C. in a homomixer, and cooling the resulting emulsion to 30° C.

TABLE 2

Effects of storage temperatures on the propagation of cells in a microbially contaminated lotion.

| | Temperature for 14 days of storage (°C.) | | | | | | |
| --- | --- | --- | --- | --- | --- | --- | --- |
| | −5 | 0 | 5 | 10 | 15 | 20 | 25 | 30 |
| Number of bacilli | 1.5 | 1.5 | 1.5 | 1.6 | 2.1 | 4.8 | 18.5 | 30.8 |
| | | | | | | | | ($\times 10^6$/ml) |

EXPERIMENT EXAMPLE 2

Study of the effects of temperatures on the viscosity and hardness of a cosmetic preparation upon the feeling sensed by its user:

The deterioration and decomposition of a cosmetic preparation usually occur as a result of the propagation of microorganisms in it. Experiments were, however, made to study the effects of temperatures on the viscosity and hardness of a cream in an environment free of any microbial contamination.

The cosmetic preparations are generally W/O or O/W emulsions obtained by the emulsification of their oily and aqueous constituents in the presence of an emulsifying agent. It is well known that emulsification depends on temperature. Many cosmetic preparations, such as creams, however, further contain waxes. Waxes are solids at normal temperatures, but are melted by heat during the process of emulsification, giving a liquid. When an emulsion is formed, they form a dispersion of solid particles which remain comparatively stable at different temperatures. Creams and other common cosmetic preparations are, however, intended for use at normal temperatures of, say, 20° C. through 25° C.. Therefore, it is likely that lower temperatures below or about 0° C. may not always be favorable from the standpoint of the rheology of e.g. a cream including its "spreading property".

Psychorheology has recently come to draw much attention. In this connection, it is of great significance to ascertain the effects which the viscosity and hardness of a semi-fluid substance may have on the factors which make a person using it feel pleasant, including its agreeableness to the touch, its moisturizing property and its softness felt on the tip of a finger.

An emollient cream was prepared from the materials shown in Table 3 in accordance with the recipe also shown in Table 3. The cream was divided into seven and was held at temperatures of 0° C., 5° C., 10° C., 15° C., 20° C., 25° C. and 30° C., respectively, for 24 hours. Then, eight persons (two males and six females, 20 through 28 years of age) were each asked to make a psychorheological evaluation of each unit of cream by taking such an amount of cream as to cover an area of about 1 $cm^2$ on the tip of his or her finger and spreading it on his or her cheek. The experiments were made in a room having a temperature of 22° C. The results are shown in Table 4. The cream which had been held at 10° C. was ranked in the first place by seven evaluators, and the cream held at 5° C. was ranked in the first place by the remaining three. It is, therefore, obvious that the cream could be held at as low a temperature as 5° C. without lowering its "spreading property" or undergoing any rheological change. The cream which had been held at 0° C. was, however, ranked in lower places, apparently because of its higher viscosity and hardness and therefore its lower "spreading property". No experiment was conducted on any cream at any temperatures below 0° C., as it would have become too hard to be appreciably "spreadable". The cream which had been stored at 15° C. or above was ranked in lower places, apparently because the evaluators did not like its "lukewarmness" or "warmness", despite its higher "spreading property".

TABLE 3

Constituents of an emollient cream and the proportions thereof.

| Kind | Constituent | Proportion (%) |
| --- | --- | --- |
| Oily constituents | Stearic acid | 14.0 |
| | Vaseline | 2.0 |
| Humectant | Propylene glycol | 10.0 |
| Emulsifying agent | Glycerol monostearate | 2.0 |
| | Polyoxyethylene sorbitan monostearate | 2.0 |
| Purified water | | 70.0 |

Process for Preparation

The cream was prepared by putting propylene glycol in purified water, heating it to 70° C., adding the other materials under stirring, subjecting the mixture to emulsification in a homomixer, and cooling the resulting emulsion to 30° C.

TABLE 4—Ranking by storage temperature of the cream in terms of "spreadability" and agreeableness of the cream to the skin.

TABLE 4

Ranking by storage temperature of the cream in terms of "spreadability" and agreeableness of the cream to the skin.

| Evaluator | Sex | Age | Ranking by temperature (°C.) | | | | | |
|---|---|---|---|---|---|---|---|---|
| | | | 1 | 2 | 3 | 4 | 5 | 6 |
| A | f | 20 | 10 | 5 | 15 | 0 | 20 | 30 |
| B | f | 21 | 10 | 5 | 15 | 0 | 20 | 30 |
| C | f | 21 | 10 | 5 | 0 | 15 | 20 | 30 |
| D | f | 22 | 10 | 5 | 0 | 15 | 30 | 20 |
| E | f | 22 | 5 | 10 | 15 | 0 | 20 | 30 |
| F | f | 23 | 10 | 5 | 0 | 15 | 20 | 30 |
| G | m | 24 | 5 | 10 | 0 | 15 | 30 | 20 |
| H | m | 28 | 5 | 10 | 0 | 15 | 20 | 30 |

EXPERIMENTAL EXAMPLE 3

Study of the temperature range which makes a cosmetic preparation most agreeable to the skin:

Experiments were made by using the emollient lotion which had been prepared in Experiment Example 1. The lotion was held under the same conditions as in Experiment Example 2 and was evaluated by the same evaluators. The results are shown in Table 5. The lotion which had been held at 5° C. was ranked in the first place by six evaluators, and the lotion held at 10° C. was ranked in the first place by the remaining two. The lotion which had been held at 10° C. was ranked in the second place by five evaluators, the lotion held at 5° C. was ranked in the second place by two persons, and the lotion held at 0° C. was ranked in the same place by the last one who was a man. There was, however, ranked in no more than the third place by all of the women the lotion which had been stored at 0° C., apparently because it was too cold. The lotion which had been held at 15° C. or above was ranked in the fourth place. No experiment was made for the evaluation of the lotion stored at any temperature below 0° C., as it would have been frozen and thus could not be used.

Three sets of experiments were made to determine the effects which the temperatures employed for the storage of the cosmetic preparations might have on (1) their preservation, (2) their "spreading property", and (3) their "coolness" agreeable to the skin, respectively, as hereinabove described. The results of these experiments obviously teach that, once its sealed package has been opened, it is advisable to store any ordinary cosmetic preparation at temperatures of 5° C. through 10° C., which are somewhat higher than what is considered appropriate for the storage of food.

TABLE 5—Ranking by storage temperature of the lotion in terms of its agreeableness to the skin.

TABLE 5

Ranking by storage temperature of the lotion in terms of its agreeableness to the skin.

| Evaluator | Sex | Age | Ranking by temperature (°C.) | | | | | |
|---|---|---|---|---|---|---|---|---|
| | | | 1 | 2 | 3 | 4 | 5 | 6 |
| A | f | 20 | 10 | 5 | 0 | 15 | 20 | 30 |
| B | f | 21 | 5 | 10 | 0 | 15 | 20 | 30 |
| C | f | 21 | 5 | 10 | 0 | 20 | 15 | 30 |
| D | f | 22 | 5 | 10 | 0 | 20 | 15 | 30 |
| E | f | 22 | 10 | 5 | 0 | 15 | 20 | 30 |
| F | f | 23 | 5 | 10 | 0 | 15 | 20 | 30 |
| G | m | 24 | 5 | 10 | 0 | 20 | 15 | 30 |

As is obvious from the foregoing, the refrigerator according to the present invention has a variety of advantages as will hereinafter be summarized:

(1) It can keep any cosmetic preparation, particularly one already in use, at an optimum temperature to protect it against any deterioration or decomposition resulting from its microbial contamination with microorganisms such as bacteria or fungi, while ensuring that it be agreeable to the skin by obtaining such a temperature condition;

(2) It is so small and handy for transportation to any desired places as to be particularly suitable for exclusive storage of cosmetic or like preparations;

(3) As its outer surfaces are decorated in a variety of ornamental patterns, the refrigerator can be put on a dressing table, or the like without spoiling the fashionable and gorgeous appearance of its environment;

(4) It enables the orderly storage of various kinds of cosmetic preparations, particularly with the aid of the removable device which can divide the interior of the refrigerator into a number of compartments. Thus, it has become much more convenient in using the refrigerator; and (5) Its door or cover may be provided either at the top of its storage chamber, or on one side thereof.

Figure 6:
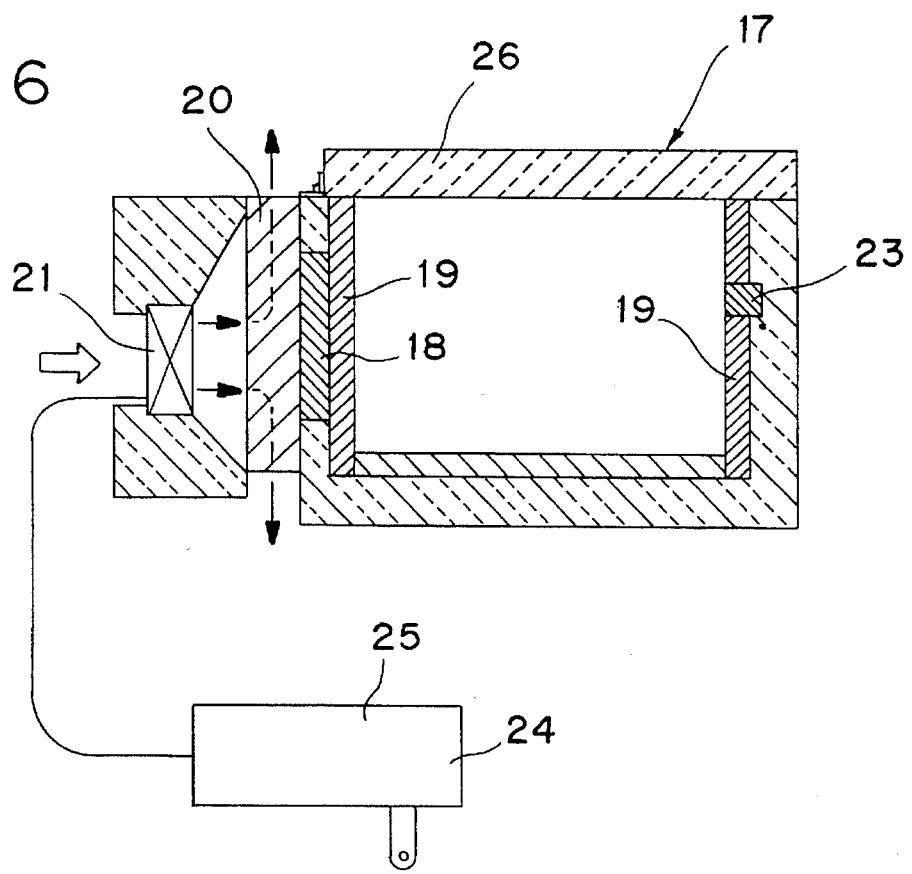
FIG. 6 is another embodiment of a compact refrigerator according to the present invention.
Figure 7:
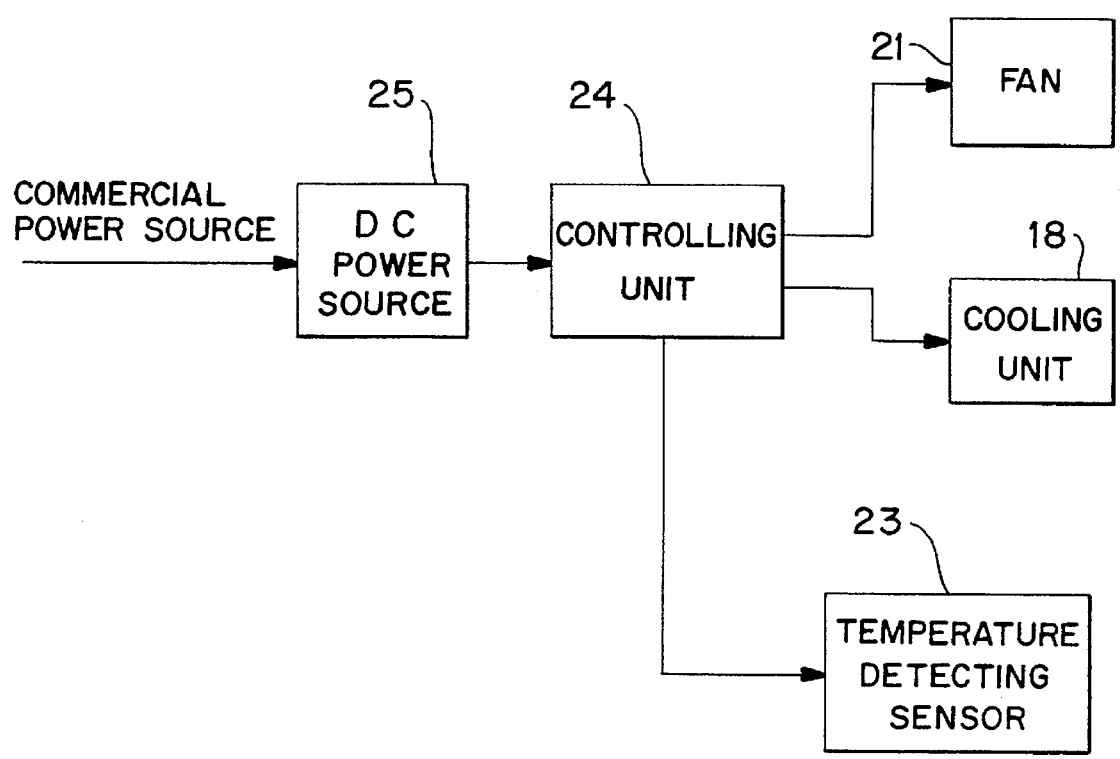
FIG. 7 is a block diagram of the compact refrigerator shown in FIG. 6.

FIG. 6 shows another embodiment of a small refrigerator according to the present invention. FIG. 7 is a block diagram of the small refrigerator shown in FIG. 6.

The small refrigerator shown in FIGS. 6 and 7 is capable of maintaining the temperature in the enclosed space thereof within a desired range of temperature and of reducing noises produced by a cooling fan thereof. Further, it is capable of maintaining the temperature uniform in the compartment of the small refrigerator and keeping uniformly and stably cold temperature at any points therein.

The box 17 made of heat insulating materials is provided at the top portion thereof with a lid 26 which is freely opened and closed, so that things can be freely put thereinto or taken therefrom. The dimensions of the enclosed space of the box 17 are 180 mm in width, 100 mm in depth and 165 mm in height. The lid 26 can be provided either at the top portion or the sidewall portion of the box 17. A cooling unit 18 is comprised with thermoelectric modules, such as, for example, Peltier elements. Cooling plates 19 are formed at the inner walls of the box 17 and are made of good heat conducting materials such as copper or aluminum. The cooling plates 19 are disposed so as to contact the cooling unit 18. The lid 26 and the bottom portion of the enclosed space made of the cooling plate 19 and the like are covered with, for example, plastics of low heat-conducting material. A heat dissipating plate 20 is made of materials of good heat conducting materials in the same way as the cooling plate 19. The cooling plate is made to have a broad surface. The cooling fan 21 takes in air from the left-hand side of the figure and pushes out the air to the cooling plate 20, thereby dissipating heat therefrom. A temperature detecting sensor 23 includes: for example, a thermistor. Although with this embodiment of the present invention, a controlling unit 24 and a DC power source 25 are constructed separately from the box 17, they can be combined with the box together as one unit. The controlling unit 25 controls the cooling unit 18 and the heat dissipating fan in response to output signals from the temperature detecting sensor so that the temperature in the compartment is maintained within a temperature range of 5° C. through 10° C.

FIG. 7 shows a block diagram of a small refrigerator shown in FIG. 6. In FIG. 7, the cooling unit 18 as a thermoelectric element, the heat dissipating fan 21 and the temperature detecting sensor 23 are the same as in FIG. 6. Numeral 24 is a controlling unit which comprises a microcomputer and the like. The power source unit 25 supplies all the portions of the device with desired direct currents and is provided with functions for receiving direct current electric power from a car and the like or alternating current electric power of 100 volts.

The controlling unit 24 comprising a microcomputer and the like is supplied with signals from the temperature detecting sensor 23 as input signals and operates to supply electric power from the DC power source unit 25 to the fan 21 and the cooling unit 18 comprising a thermoelectric element, as desired. Instead of operating the cooling unit 18 and the fan 21 by means of the controlling unit 25 in response to output signals from the temperature detecting sensor 23, the controlling unit 25 is also capable of intermittently operating either the cooling unit 18 or the fan 21 while always driving the other one.

One of the features of the present invention is that the dimensions of the heat dissipating plate for dissipating heat is designed by taking into balance of heat quantity as a design condition. For example, in practice, assuming that maximum heat quantity entering into the compartment of the cooling box 17 from the outside thereof is $Q_1$(Kcal/H) and natural heat dissipation capacity of the heat dissipating plate 20 is $Q_0$(Kcal/H), it is designed to meet a condition $Q_1=Q_0$.

Air quantity produced by the fan 21 is determined so as to provide a capacity of, for example, $3Q_0$ when the heat dissipating plate 20 is cooled compulsorily by means of the cooling fan 21. As a result, cooling heat quantity given to goods stored in the cooling box 17 will be substantially more than $2Q_0$(Kcal/H). The present invention comprises the constituent elements as in the foregoing. Since $Q_0$ is determined with respect to heat quantity $Q_1$ (Kcal/H) to be dissipated, the temperature in the interior of the cooling box 17 will be constant due to natural heat dissipation if the lid 26 is not opened.

When goods kept in the cooling box 17 are not cooled at a desired temperature, or the temperature in the interior of the cooling box rises as the lid 26 of the cooling box 17 is opened, the fan 21 is driven so that the compartment of the cooling box 17 can be cooled with cooling heat quantity of more than $2Q_0$(Kcal/H).

Since the fan 21 is driven only when cooling heat quantity of more than $2Q_0$ is required, a cooling box producing no noises can be provided in a normal state in which the fan 21 is not operated.

With the present invention, balance in heat quantity is taken into consideration to a possible maximum extent. As a result, natural heat dissipation and compulsory heat dissipation can be used so that there can be simultaneously solved a problem of realizing and maintaining a desired temperature and another problem of eliminating noises, with this problem conflicting with the temperature realizing problem. A compact refrigerator according to the present invention is not limited to store cosmetics as goods to be stored therein. The refrigerator is also capable of keeping any goods at a desired temperature, as required. Also, since the cooling box according to the present invention is small-sized and easily transferable, it is very convenient to use.

Figure 8:
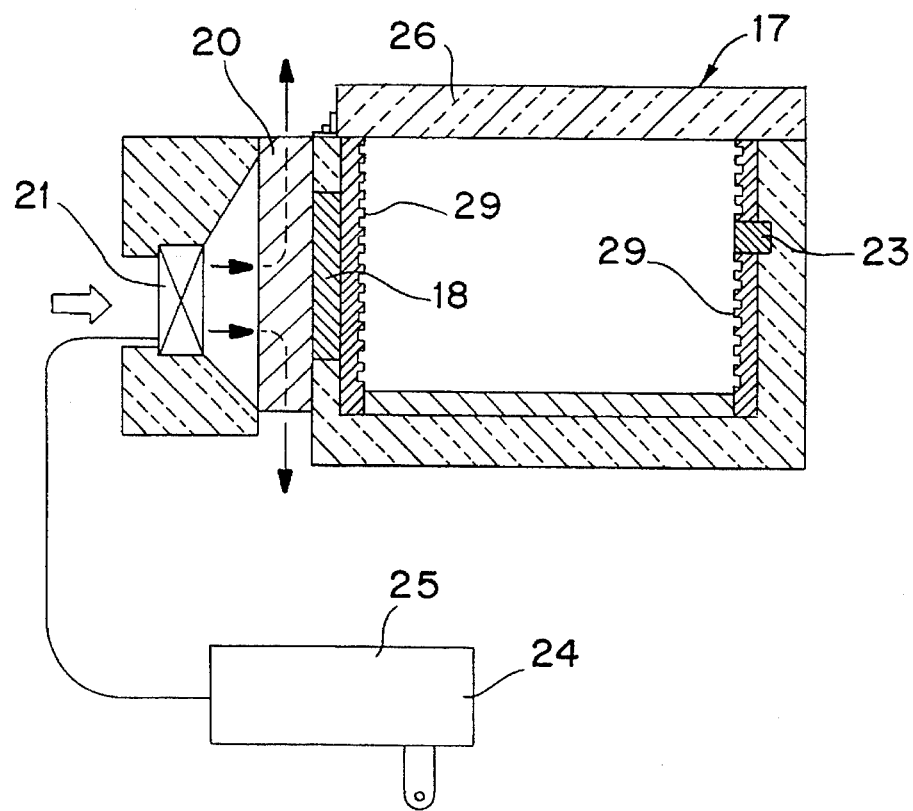
FIG. 8 is another embodiment of a small refrigerator according to the present invention.

FIG. 8 is an another embodiment of a compact refrigerator according to the present invention. The difference between the embodiment shown in FIG. 8 and the one shown in FIG. 6 is that the embodiment shown in FIG. 6 uses the cooling plate in a planar form, while the embodiment shown in FIG. 8 uses a cooling plate 29 in a concave-convex form. The other portions or the other part of the construction of the small refrigerator shown in FIG. 6 are identical with corresponding ones of the refrigerator shown in FIG. 8. If the cooling plate is shaped in a concave-convex form, the dimensions of the surface of the cooling plate 29 is increased so that cooling efficiency is improved and the dimensions of the cooling plate directly contacting the goods disposed in the interior of the cooling box 17 are minimized, which is complied with a feature of the present invention for preventing temperature irregularities from being produced. Thus, it is preferable to shape the cooling plate in a concave-convex form, but the cooling plate in a planar form can also be used without any inconveniences.

The embodiments shown in FIG. 6 through FIG. 8 have features as in the following: (1) It is constructed to utilize compulsory heat dissipation in addition to natural heat dissipation. At first, natural heat dissipation with the heat dissipating plate is used. When the temperature rises beyond the limit, the fan is driven to provide compulsory heat dissipation. (2) The fan for compulsory heat dissipation is driven for a predetermined time period to lower the temperature below a desired temperature after the lid of the cooling box is closed. Further, when the temperature outside the cooling box is not within a predetermined temperature range, the fan is continuously driven. In this case, balance of heat quantity is taken into consideration to design the dimensions of the heat dissipation plate as a design condition. (3) An object of the present invention is to prevent different temperatures from being produced at different portions of goods stored in the cooling box by devising a shape of the cooling plate disposed in the box.

The foregoing object of the present invention is achieved by disposing cooling plates having good heat conductivity and shaped in a planar form or in a concave-convex form along the inside wall of the box so that the cooling plate contacts the cooling unit of the box having the lid to be opened or closed, by disposing a heat dissipating plate on the exterior side of the cooling unit and by disposing a heat dissipating fan on the left-hand side of the heat dissipating plate and by having a temperature sensing sensor in the box, with the cooling plate, the fan and the temperature sensor being controlled by the controlling unit. The bottom surface of the interior of the cooling box is covered with plastics of low heat conductivity.

It should be noted that although in the foregoing embodiment the heat dissipating fan 21 is used to promote heat dissipation operation made by the heat dissipating plate 20, it is also possible to maintain the temperature in the compartment of a small refrigerator within a desired temperature range without using the heat dissipating fan 21.

It should be noted that although in the foregoing embodiment the cooling unit 18 and the heat dissipation fan 21 are controlled in response to output signals from the temperature detecting sensor, it is also possible to control one of the cooling unit 18 and the heat dissipation fan 21 to be driven in response to output signals from the temperature detecting sensor while the other one is driven all the time.

It should be noted that the foregoing embodiments are only some embodiments in accordance with the present invention. It is apparent that other embodiments or other modifications can be easily presented without departing the spirit and scope of the present invention.

We claim:

1. A compact refrigerator for storing virtually preservative-free cosmetic preparations, comprising:

chamber means, including a top portion, a sidewall portion, and a bottom portion, for storing the virtually preservative-free cosmetic preparations, and temperature means for maintaining a temperature of said chamber means and the virtually preservative-free cosmetic preparations within a temperature range of 6° C. through 10° C.

2. The compact refrigerator of claim 1, wherein the virtually preservative-free cosmetic preparations contain only a small amount of a chemical preservative or disinfectant, so that any bad effect produced by the chemical preservative or disinfectant on a human body is minimized.

3. The compact refrigerator of claim 1, wherein the virtually preservative-free cosmetic preparations do not contain any chemical preservative or disinfectant.

4. A compact refrigerator having a chamber for storing virtually preservative-free cosmetic preparations, said chamber including a top portion, a sidewall portion, and a bottom portion, said compact refrigerator comprising:

a cooling device provided in said sidewall portion;

a cooling plate located inside said sidewall portion and contacting said cooling device;

a heat dissipating plate located outside said cooling device said heat dissipating plate have a natural heat dissipation capacity of $Q_0$ cal/sec;

a fan for promoting dissipation of heat by said heat dissipating plate;

a cover forming said top portion wherein when said cover is opened, a maximum heat quality of $Q_1$ cal/sec enters said compact refrigerator, wherein $Q_1=Q_0$;

a temperature sensor for detecting a temperature of said chamber; and control means for controlling said cooling device and/or said fan in response to an output signal of said temperature sensor by driving said fan only when greater than $2Q_0$ cal/sec are required in order to keep the temperature of said chamber and a temperature of the virtually preservative-free cosmetic preparations at a specific temperature or within a specific temperature range to prevent microbial contamination of the virtually preservative-free cosmetic preparations.

5. The compact refrigerator for storing virtually preservative-free cosmetic preparations of claim 4, wherein the temperature of said chamber is kept within the specific range of about 5° C. through 10° C.

6. The compact refrigerator of claim 4, wherein the temperature of said chamber is kept at the specific temperature of about 7° C.

7. The compact refrigerator of claim 4, wherein said cooling device includes a thermoelectric element.

8. The compact refrigerator of claim 4, wherein the cooling plate is made of material of good heat conductivity and is shaped in a flat form or in a concave-convex form.

9. A compact refrigerator including a chamber for storing virtually preservative-free cosmetic preparations, said chamber including a top portion, a sidewall portion, and a bottom portion, said refrigerator comprising:

a cooling device provided in said sidewall portion;

a cooling plate located inside said sidewall portion and contacting said cooling device;

a heat dissipating plate located inside said cooling device said heat dissipating plate have a natural heat dissipation capacity of $Q_0$ cal/sec;

a cover forming said top portion wherein when said cover is opened, a maximum heat quality of $Q_1$ cal/sec enters said compact refrigerator, wherein $Q_1=Q_0$;

a temperature sensor for detecting a temperature in said chamber; and control means for controlling said cooling device in response to an output signal of said temperature sensor by driving said fan only when greater than $2Q_0$ cal/sec are required in order to keep the temperature of said chamber and a temperature of the virtually preservative-free cosmetic preparations at a specific temperature or with a specific temperature range to prevent microbial contamination of the virtually preservative-free cosmetic preparations.

10. A small refrigerator for storing virtually preservative-free cosmetic preparations, comprising:

a storage chamber defined by a top portion, a sidewall portion, and a bottom portion, for keeping the virtually preservative-free cosmetic preparations, the virtually preservative-free cosmetic preparations containing only a small amount of a chemical preservative or disinfectant, so that any bad effect produced by the chemical preservative or disinfectant on a human body is minimized, and temperature control means for preventing microbial contamination of the virtually preservative-free cosmetic preparations.

11. A small refrigerator for storing virtually preservative-free cosmetic preparations, comprising:

a storage chamber for keeping the virtually preservative-free cosmetic preparations, the cosmetic preparations not containing any chemical preservative or disinfectant, and temperature control means for preventing microbial contamination of the virtually preservative-free cosmetic preparations.

12. A method of optimizing storage of virtually preservative-free cosmetic preparations, comprising the steps of:

(a) providing a chamber, including a top portion, a sidewall portion, and a bottom portion, for storing the virtually preservative-free cosmetic preparations, and (b) maintaining a temperature of the chamber and the virtually preservative-free cosmetic preparations within a temperature range of 6° C. through 10° C.

13. The method of claim 12, wherein the virtually preservative-free cosmetic preparations contain only a small amount of a chemical preservative or disinfectant, so that any bad effect produced by the chemical preservative or disinfectant on a human body is minimized.

14. The method of claim 12, wherein the virtually preservative-free cosmetic preparations do not contain any chemical preservative or disinfectant.

15. A method of optimizing storage of virtually preservative-free cosmetic preparations in a chamber, the chamber including a cover forming a top portion, a sidewall portion, and a bottom portion, wherein when said cover is opened, a maximum heat quality of $Q_1$ cal/sec enters said compact refrigerator, wherein $Q_1=Q_0$ said method comprising the steps of:

(a) providing a cooling device in the sidewall portion;

(b) locating a cooling plate inside the sidewall portion and contacting the cooling device;

(c) locating a heat dissipating plate outside the cooling device said heat dissipating plate have a natural heat dissipation capacity of $Q_0$ cal/sec;

(d) providing a fan for promoting dissipation of heat from the heat dissipating plate;

(e) detecting a temperature of the chamber with a temperature sensor; and (f) controlling the cooling device and/or the fan in response to temperature detected in said step (e) by driving said fan only when greater than $2Q_0$ cal/sec are required in order to keep the temperature of the chamber and a temperature of the virtually preservative-free cosmetic preparations at a specific temperature or within a specific temperature range to prevent microbial contamination and optimize the storage of the virtually preservative-free cosmetic preparations.

16. The method of claim 15, wherein the temperature of the chamber is kept within the specific range of about 5° C. through 10° C.

17. The method of claim 15, wherein the temperature of the chamber is kept at the specific temperature of about 7° C.

18. The method of claim 15, wherein the cooling device includes a thermoelectric element.

19. The method of claim 15, wherein the cooling plate is made of material of good heat conductivity and is shaped in a flat form or in a concave-convex form.

20. A method of optimizing storage of virtually preservative-free cosmetic preparations in a chamber, the chamber including a cover forming a top portion, a sidewall portion, and a bottom portion, wherein when said cover is opened, a maximum heat quality of $Q_1$ cal/sec enters said compact refrigerator, wherein $Q_1=Q_0$ said method comprising the steps of:

(a) providing a cooling device in the sidewall portion;

(b) locating a cooling plate inside the sidewall portion and contacting the cooling device;

(c) locating a heat dissipating plate inside the cooling device said heat dissipating plate have a natural heat dissipation capacity of $Q_0$ cal/sec;

(d) detecting a temperature in said chamber with a temperature sensor; and (e) controlling the cooling device in response to the temperature detected in said step (d) by driving said fan only when greater than $2Q_0$ cal/sec are required in order to keep the temperature of said chamber and a temperature of the virtually preservative-free cosmetic preparations at a specific temperature or with a specific temperature range to prevent microbial contamination and optimize the storage of the virtually preservative-free cosmetic preparations.

21. A method of optimizing storage of virtually preservative-free cosmetic preparations, comprising the steps of:

(a) providing a storage chamber defined by a top portion, a sidewall portion, and a bottom portion, for keeping the virtually preservative-free cosmetic preparations, the virtually preservative-free cosmetic preparations containing only a small amount of a chemical preservative or disinfectant, so that any bad effect produced by the chemical preservative or disinfectant on a human body is minimized, and (b) preventing microbial contamination of the virtually preservative-free cosmetic preparations.

22. A method of optimizing storage of virtually preservative-free cosmetic preparations, comprising the steps of:

(a) providing a storage chamber for keeping the virtually preservative-free cosmetic preparations, the cosmetic preparations not containing any chemical preservative or disinfectant, and (b) preventing microbial contamination of the virtually preservative-free cosmetic preparations.

23. The small refrigerator of claim 10, wherein said temperature control means prevents microbial contamination by keeping the virtually preservative-free cosmetic preparations within a temperature range of 5° C. to 10° C.

24. The small refrigerator of claim 11, wherein said temperature control means prevents microbial contamination by keeping the virtually preservative-free cosmetic preparations within a temperature range of 5° C. to 10° C.

25. The method of claim 21, wherein said step (b) prevents microbial contamination by keeping the virtually preservative-free cosmetic preparations within a temperature range of 5° C. to 10° C.

26. The method of claim 22, wherein said step (b) prevents microbial contamination by keeping the virtually preservative-free cosmetic preparations within a temperature range of 5° C. to 10° C.

* * * * *